US007060727B2

(12) United States Patent
Gallop

(10) Patent No.: US 7,060,727 B2
(45) Date of Patent: Jun. 13, 2006

(54) PRODRUGS OF FUSED GABA ANALOGS, PHARMACEUTICAL COMPOSITIONS AND USES THEREOF

(75) Inventor: Mark A. Gallop, Los Altos, CA (US)

(73) Assignee: XenoPort, Inc., Santa Clara, CA (US)

( * ) Notice: Subject to any disclaimer, the term of this patent is extended or adjusted under 35 U.S.C. 154(b) by 104 days.

(21) Appl. No.: 10/734,689

(22) Filed: Dec. 11, 2003

(65) Prior Publication Data

US 2004/0147455 A1    Jul. 29, 2004

Related U.S. Application Data

(60) Provisional application No. 60/433,216, filed on Dec. 12, 2002, provisional application No. 60/432,871, filed on Dec. 11, 2002.

(51) Int. Cl.
*A61K 31/27* (2006.01)
*C07C 271/22* (2006.01)

(52) U.S. Cl. ............ 514/480; 514/354; 514/452; 514/461; 546/322; 549/372; 549/450; 560/28

(58) Field of Classification Search ............ 560/28; 549/372, 450; 546/322; 514/354, 452, 461, 514/480
See application file for complete search history.

(56) References Cited

U.S. PATENT DOCUMENTS

| | | | |
|---|---|---|---|
| 3,845,770 | A | 11/1974 | Theeuwes et al. |
| 3,916,899 | A | 11/1975 | Theeuwes et al. |
| 4,024,175 | A | 5/1977 | Satzinger et al. |
| 4,087,544 | A | 5/1978 | Satzinger et al. |
| 5,084,479 | A | 1/1992 | Woodruff |
| 5,112,598 | A | 5/1992 | Biesalski |
| 5,556,611 | A | 9/1996 | Biesalski |
| 5,563,175 | A | 10/1996 | Silverman et al. |
| 5,698,155 | A | 12/1997 | Grosswald et al. |
| 6,001,876 | A | 12/1999 | Singh |
| 6,020,370 | A | 2/2000 | Horwell et al. |
| 6,028,214 | A | 2/2000 | Silverman et al. |
| 6,103,932 | A | 8/2000 | Horwell et al. |
| 6,117,906 | A | 9/2000 | Silverman et al. |
| 6,596,900 | B1 | 7/2003 | Blakemore et al. |

FOREIGN PATENT DOCUMENTS

| | | |
|---|---|---|
| WO | WO 92/09560 A1 | 6/1992 |
| WO | WO 93/23383 A1 | 11/1993 |
| WO | WO 97/29101 A1 | 8/1997 |
| WO | WO 97/33858 A1 | 9/1997 |
| WO | WO 97/33859 A1 | 9/1997 |
| WO | WO 98/17627 A1 | 4/1998 |
| WO | WO 99/08671 A1 | 2/1999 |
| WO | WO 99/21824 A1 | 5/1999 |
| WO | WO 99/31057 A1 | 6/1999 |
| WO | WO 99/31074 A2 | 6/1999 |
| WO | WO 99/31074 A3 | 6/1999 |
| WO | WO 99/31075 A1 | 6/1999 |
| WO | WO 99/37296 A1 | 7/1999 |
| WO | WO 99/61424 A1 | 12/1999 |
| WO | WO 00/23067 A1 | 4/2000 |
| WO | WO 00/31020 A1 | 6/2000 |
| WO | WO 00/50027 A1 | 8/2000 |
| WO | WO 01/28978 A1 | 4/2001 |
| WO | WO 02/00209 A2 | 1/2002 |
| WO | WO 02/00209 A3 | 1/2002 |
| WO | WO 00/15611 A1 | 3/2002 |
| WO | WO 02/085839 A1 | 10/2002 |
| WO | WO 02/090318 A1 | 11/2002 |

OTHER PUBLICATIONS

U.S. Appl. No. 10/171,485, Gallop et al.
U.S. Appl. No. 10/170,127, Cundy et al.
U.S. Appl. No. 10/167,797, Gallop et al.
Alderman, "A Review of Cellulose Ethers in Hydrophilic Matrices or Oral controlled-Release Dosage Forms," *Int. J. Pharm. Tech. & Prod. Mfr.* 1984, 5(3) 1-9.
Bamba et al., "Release Mechanisms in Gelforming Sustained Release Preparation," *Int. J. Pharm*. 1979, 2, 307.
Bryans et al., "3-Substituted GABA Analogs with Central Nervous System Activity: A Review," *Med. Res. Rev*. 1999, 19, 149-177.
During et al., "Controlled release of dopamine from a polymeric brain implant: in vivo characterization," 1989, *Ann. Neurol*. 25:351.
Goodson, "Medical Applications of Controlled Release," vol. 2, pp. 115-138 (1984).
Howard et al., "Intercerebral Drug Delivery in Rats with Lesion-Induced Memory Deficits," 1989, *J. Neurosurg*. 71:105-112.
Jezyk et al., "Transport of Pregabalin in Rat Intestine and Caco-2 Monolayers," *Pharm. Res*. 1999, 16, 519-526.
Langer et al., "Chemical and Physical Structure of Polymers as Carriers for Controlled Release of Bioactive Agents: A Review," *J Macromol. Sci. Rev. Macromol. Chem*. 1983, 23:61.
Langer, "New Method of Drug Delivery," 1990, *Science* 249:1527-1533.
Levy et al., "Inhibition of Calcification of Bioprosthetic Heart Valves by Local Controlled-Release Diphosphonate," *Science* 1985 228: 190-192.
Magnus, "Nonepileptic Uses of Gabapentin," *Epilepsia*, (40) (Suppl. 6): S66-S72 (1999).

(Continued)

*Primary Examiner*—Bernard Dentz
(74) *Attorney, Agent, or Firm*—Dorsey & Whitney LLP; Richard F. Trecartin; Timothy A. Worrall

(57) ABSTRACT

The present invention relates generally to prodrugs of fused GABA analogs, pharmaceutical compositions of prodrugs of fused GABA analogs, methods of making prodrugs of fused GABA analogs and methods of using prodrugs of fused GABA analogs and pharmaceutical compositions of prodrugs of fused GABA analogs to treat or prevent various diseases.

22 Claims, No Drawings

OTHER PUBLICATIONS

Saudek et al., "A Preliminary Trial of the Programmable Implantable Medication System for Insulin Delivery," *N. Engl. J. Med.*, 1989, 321: 574.

Sefton, "Implantable Pumps," *CRC Crit Ref Biomed. Eng.* 1987, 14:201.

Verma et al., "Osmotically Controlled Oral Drug Delivery," *Drug Dev. Ind. Pharm.*, 2000, 26:695-708.

PRODRUGS OF FUSED GABA ANALOGS, PHARMACEUTICAL COMPOSITIONS AND USES THEREOF

This application claims the benefit under 35 U.S.C. § 119(e) from U.S. Provisional Application Ser. No. 60/432,871 filed Dec. 11, 2002, and U.S. Provisional Application Ser. No. 60/433,216 filed Dec. 12, 2002, which are herein incorporated by reference, in their entirety.

1. FIELD OF THE INVENTION

The present invention relates generally to prodrugs of fused GABA analogs, pharmaceutical compositions of prodrugs of fused GABA analogs, methods of making prodrugs of fused GABA analogs and methods of using prodrugs of fused GABA analogs and pharmaceutical compositions of prodrugs of fused GABA analogs to treat or prevent various diseases.

2. BACKGROUND OF THE INVENTION

Gamma ("γ")-aminobutyric acid ("GABA") is one of the major inhibitory transmitters in the central nervous system of mammals. GABA is not transported efficiently into the brain from the bloodstream because of poor transport properties that prevent passage through the blood-brain barrier. Consequently, brain cells synthesize virtually all of the GABA found in the brain (by decarboxylation of glutamic acid with pyridoxal phosphate).

GABA regulates neuronal excitability through binding to specific membrane proteins (i.e., GABAA receptors), which results in opening of an ion channel. The entry of chloride ion through the ion channel leads to hyperpolarization of the recipient cell, which consequently prevents transmission of nerve impulses to other cells. Low levels of GABA have been observed in individuals suffering from epileptic seizures, motion disorders (e.g., multiple sclerosis, action tremors, tardive dyskinesia), panic, anxiety, depression, alcoholism and manic behavior.

The presence of low amounts of GABA in a number of common disease states has stimulated intensive interest in preparing GABA analogs, which may have superior pharmaceutical properties in comparison to GABA (e.g., the ability to cross the blood brain barrier). Accordingly, a number of GABA analogs, with considerable International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Belliotti et al., International Publication No. WO 99/31074; Bryans et al., International Publication No. WO 99/31075; Bryans et al., International Publication No. WO 99/61424; Bryans et al., International Publication No. WO 00/15611; Bryans, International Publication No. WO 00/31020; Bryans et al., International Publication No. WO 00/50027; and Bryans et al., International Publication No. WO 02/00209).

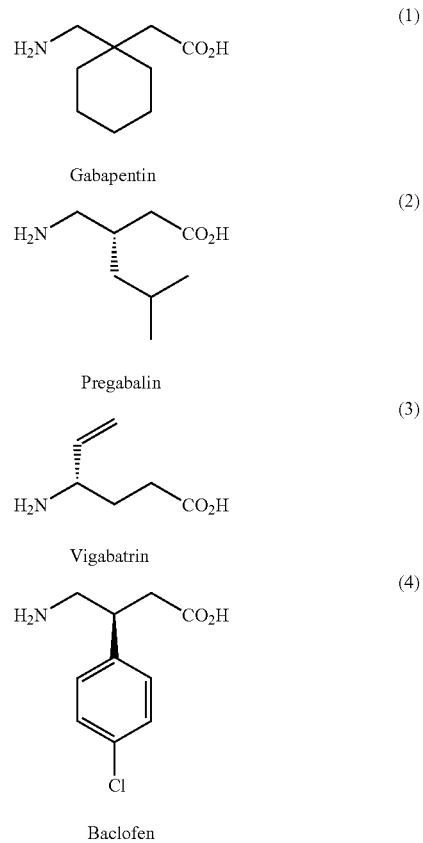

Pharmaceutically important GABA analogs include, for example, gabapentin (1), pregabalin (2), vigabatrin (3), and baclofen (4) shown above. Gabapentin is a lipophilic GABA analog that can pass through the blood-brain barrier, which has been used to clinically treat epilepsy since 1994. Gabapentin also has potentially useful therapeutic effects in chronic pain states (e.g., neuropathic pain, muscular and skeletal pain), psychiatric disorders (e.g., panic, anxiety, depression, alcoholism and manic behavior), movement disorders (e.g., multiple sclerosis, action tremors, tardive dyskinesia), etc. (Magnus, *Epilepsia* 1999, 40:S66–S72).

New classes of GABA analogs, which are bicyclic amino acid derivatives have recently been described (Bryans et al., International Publication No. WO 01/28978; Blakemore et al., International Publication No. WO 02/085839; Blakemore et al., U.S. Pat. No. 6,596,900; Blakemore et al., International Publication No. WO 02/090318). Like other GABA analogs, these compounds are useful medicaments for the treatment or prevention of epilepsy, depression, anxiety, psychosis, faintness attacks, hypokinesia, cranial disorders, neurodegenerative disorders, panic, pain, inflammatory disease, insomnia, gastrointestinal disorders and ethanol withdrawal syndrome.

Rapid systemic clearance and/or poor oral bioavailability are significant problems with many GABA analogs such as gabapentin, which consequently require frequent dosing to maintain a therapeutic or prophylactic concentration in the systemic circulation (Bryans et al., *Med. Res. Rev.* 1999, 19, 149–177). For example, dosing regimens of 300–600 mg doses of gabapentin administered three times per day are typically used for anticonvulsive therapy. Higher doses (1800–3600 mg/d in divided doses) are typically used for the treatment of neuropathic pain states.

Sustained released formulations are a conventional solution to the problem of rapid systemic clearance, as is well known to those of skill in the art (See, e.g., "Remington's Pharmaceutical Sciences," Philadelphia College of Pharmacy and Science, 19th Edition, 1995). Osmotic delivery systems are also recognized methods for sustained drug delivery (See, e.g., Verma et al., *Drug Dev. Ind. Pharm.* 2000, 26:695–708). Many GABA analogs are not absorbed via the large intestine but rather are typically absorbed in the small intestine by the large neutral amino acid transporter ("LNAA") (Jezyk et al., *Pharm. Res.* 1999, 16, 519–526). The rapid passage of conventional dosage forms through the proximal absorptive region of the gastrointestinal tract has prevented the successful application of sustained release technologies to many GABA analogs.

Thus, there is a significant need for more readily orally absorbable versions of GABA analogs and effective sustained release versions of GABA analogs to minimize increased dosing frequency due to rapid systemic clearance, particularly of fused GABA analogs.

3. SUMMARY OF THE INVENTION

The present invention satisfies these and other needs by providing prodrugs of fused GABA analogs, pharmaceutical compositions of prodrugs of fused GABA analogs, methods of making prodrugs of fused GABA analogs and methods of using prodrugs of fused GABA analogs and pharmaceutical compositions of prodrugs of fused GABA analogs to treat or prevent various diseases.

In a first aspect, the present invention provides compounds of structural formula (I):

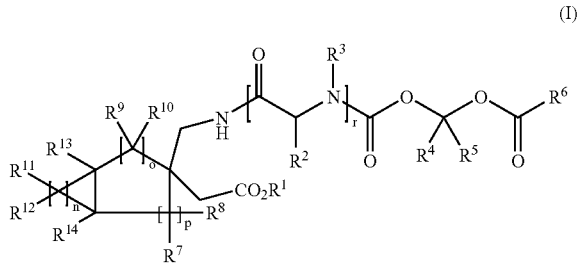

(I)

or a pharmaceutically acceptable salt, hydrate, solvate or N-oxide thereof, wherein:

n is 1, 2, 3, 4, 5 or 6;
o is 0, 1, 2 or 3;
p is 0, 1 or 2;
r is 0 or 1;
$R^1$ and $R^3$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;
$R^2$ is hydrogen, alkyl, substituted alkyl, alkoxy, substituted alkoxy, acyl, substituted acyl, acylamino, substituted acylamino, alkylamino, substituted alkylamino, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, dialkylamino, substituted dialkylamino, heteroalkyl, substituted heteroalkyl, heteroaryl, substituted heteroaryl, heteroarylalkyl, substituted heteroarylalkyl, oxycarbonyl or substituted oxycarbonyl, or optionally, $R^2$ and $R^3$ together with the atoms to which they are bonded form a cycloheteroalkyl or substituted cycloheteroalkyl ring;
$R^4$ and $R^5$ are independently hydrogen, alkyl, substituted alkyl, aryl, substituted aryl, arylalkyl, substituted arylalkyl, carbamoyl, substituted carbamoyl, cycloalkyl, substituted cycloalkyl, cycloalkoxycarbonyl, substituted cycloalkoxycarbonyl, heteroalkyl, substituted heteroalkyl, heteroaryl, substituted heteroaryl, heteroarylalkyl, substituted heteroarylalkyl, oxycarbonyl or substituted oxycarbonyl or optionally, $R^4$ and $R^5$ together with the carbon atom to which they are bonded form a cycloalkyl, substituted cycloalkyl, cycloheteroalkyl or substituted cycloheteroalkyl ring;
$R^6$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl; and
each of $R^7$, $R^8$, $R^9$, $R^{10}$, $R^{11}$, $R^{12}$, $R^{13}$ and $R^{14}$ is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

In a second aspect, the present invention provides pharmaceutical compositions, which generally comprise one or more compounds of the invention, pharmaceutically acceptable salts, hydrates, solvates or N-oxides thereof and a pharmaceutically acceptable vehicle such as a diluent, carrier, excipient or adjuvant. The choice of diluent, carrier, excipient and adjuvant will depend upon, among other factors, the desired mode of administration.

In a third aspect, the present invention provides methods for treating or preventing various diseases or disorders. The methods generally involve administering to a patient in need of such treatment or prevention a therapeutically effective amount of a compound and/or pharmaceutical composition of the invention.

4. DETAILED DESCRIPTION OF THE INVENTION

4.1 Definitions

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms, even more preferably, from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl,-but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cyclohexylcarbonyl, cyclohexylmethylcarbonyl, benzoyl, benzylcarbonyl and the like.

"Alkylamino" by itself or as part of another substituent refers to a radical —NHR$^{31}$ where R$^{31}$ represents an alkyl or cycloalkyl group as defined herein. Representative examples include, but are not limited to, methylamino, ethylamino, 1-methylethylamino, cyclohexyl amino and the like.

"Alkoxy" by itself or as part of another substituent refers to a radical —OR$^{32}$ where R$^{32}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR$^{32}$ where R$^{32}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably from 6 to 12 carbon atoms.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$–$C_{30}$) arylalkyl, e.g., the alkanyl, alkenyl or alkynyl moiety of the arylalkyl group is ($C_1$–$C_{10}$) and the aryl moiety is ($C_6$–$C_{20}$), more preferably, an arylalkyl group is ($C_6$–$C_{20}$) arylalkyl, e.g., the alkanyl, alkenyl or alkynyl moiety of the arylalkyl group is ($C_1$–$C_8$) and the aryl moiety is ($C_6$–$C_{12}$).

"Carbamoyl" by itself or as part of another substituent refers to the radical —C(O)N(R$^{33}$)R$^{34}$ where R$^{33}$ and R$^{34}$ are independently hydrogen, alkyl, substituted alkyl, aryl, substituted aryl, arylalkyl, substituted arylalkyl, heteroarylalkyl, substituted heteroarylalkyl, heteroaryl or substituted heteroaryl, as defined herein.

"Compounds of the invention" refers to compounds encompassed by the generic formulae disclosed herein and includes any specific compounds within those formulae whose structure is disclosed herein. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass conventionally found in nature. Examples of isotopes that may be incorporated into the compounds of the invention include, but are not limited to, $^2$H, $^3$H, $^{13}$C, $^{14}$C, $^{15}$N, $^{18}$O and $^{17}$O. Compounds of the invention may exist in unsolvated forms as well as solvated forms, including hydrated forms and as N-oxides. In general, the hydrated, solvated and N-oxide forms are within the scope of the present invention. Certain compounds of the present invention may exist in multiple crystalline or amorphous forms. In general, all physical forms are equivalent for the uses contemplated by the present invention and are intended to be within the scope of the present invention. Further, it should be understood, when partial structures of the compounds of the invention are illustrated, that brackets indicate the point of attachment of the partial structure to the rest of the molecule.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. Preferably, the cycloalkyl group is ($C_3$–$C_{10}$) cycloalkyl, more preferably ($C_3$–$C_7$) cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Derived from a fused GABA analog" refers to a moiety that is structurally related to a fused GABA analog. The structure of the moiety is identical to the compound except at 1 or 2 positions. At these positions, a hydrogen atom attached to the amino group, and (optionally) the hydroxyl moiety of the carboxylic acid group has been replaced with a covalent bond that serves as a point of attachment to another moiety.

"Dialkylamino" by itself or as part of another substituent refers a radical—$NR^{35}R^{36}$ where $R^{35}$ and $R^{36}$ are independently an alkyl or cycloalkyl group as defined herein. Representative examples include, but are not limited to, dimethylamino, methylethylamino, di-(1-methylethyl) amino, (cyclohexyl)(methyl)amino, (cyclohexyl)(ethyl) amino, (cyclohexyl)(propyl)amino and the like.

"Fused GABA analog" refers to a compound, unless specified otherwise, as having the following structure:

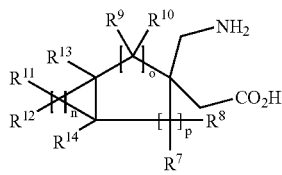

wherein:
n is 1, 2, 3, 4, 5 or 6;
o is 0, 1, 2 or 3;
p is 0, 1 or 2; and
each of $R^7$, $R^8$, $R^9$, $R^{10}$, $R^{11}$, $R^{12}$, $R^{13}$ and $R^{14}$ is independently hydrogen, alkyl substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —$NR^{37}R^{38}$—, =N—N=, —N=N—, —N=N—$NR^{39}R^{40}$, —$PR^{41}$—, —$P(O)_2$—, —$POR^{42}$—, —O—$P(O)_2$—, —SO—, —$SO_2$—, —$SnR^{43}R^{44}$— and the like, where $R^{37}$, $R^{38}$, $R^{39}$, $R^{40}$, $R^{41}$, $R^{42}$, $R^{43}$ and $R^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5–20 membered heteroaryl, more preferably from 5–10 membered heteroaryl. Preferred heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6–30 membered heteroarylalkyl, e.g., the alkanyl, alkenyl or alkynyl moiety of the heteroarylalkyl is 1–10 membered and the heteroaryl moiety is a 5–20-membered heteroaryl, more preferably, 6–20 membered heteroarylalkyl, e.g., the alkanyl, alkenyl or alkynyl moiety of the heteroarylalkyl is 1–8 membered and the heteroaryl moiety is a 5–12-membered heteroaryl.

"Oxycarbonyl" by itself or as part of another substituent refers to a radical —C(O)—$OR^{45}$ where $R^{45}$ represents an alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl substituted heteroaryl, heteroarylalkyl or substituted heteroarylalkyl group as defined herein. Representative examples include, but are not limited to, methoxycarbonyl, piperdineoxycarbonyl, phenyloxycarbonyl, benzyloxycarbonyl and the like.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Pharmaceutical composition" refers to at least one compound of the invention and a pharmaceutically acceptable vehicle, with which the compound is administered to a patient.

"Pharmaceutically acceptable salt" refers to a salt of a compound of the invention, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently, although not necessarily, pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, enamine, imine, N-phosphonyl, N-phosphoryl or N-sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1–8 (John Wiley and Sons, 1971–1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are independently replaced with the same or different substituent(s). Typical substituents include, but are not limited to, $-M$, $-R^{60}$, $-O^-$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2O^-$, $-S(O)_2OH$, $-S(O)_2R^{60}$, $-OS(O_2)O^-$, $-OS(O)_2R^{60}$, $-P(O)(O)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)$ $NR^{60}OR^{61}$, $-NR^{62}C(NR^{63})NR^{60}R^{61}$ and $-C(NR^{62})$ $NR^{60}R^{61}$ where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. Preferably, substituents include -M, —$R^{60}$, =O, —$OR^{60}$, —$SR^{60}$, —S$^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O_2)$O$^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$, more preferably, -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$, most preferably, -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

4.2 Compounds of the Invention

In a first embodiment, the present invention provides compounds of structural Formula (I):

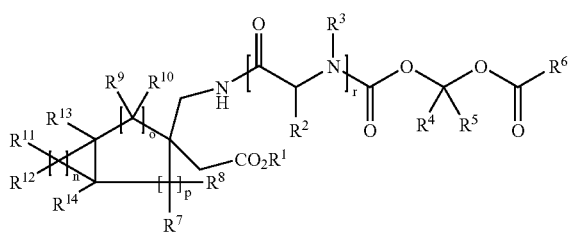

(I)

or a pharmaceutically acceptable salt, hydrate, solvate or N-oxide thereof, wherein:

n is 1, 2, 3, 4, 5 or 6;

o is 0, 1, 2 or 3;

p is 0, 1 or 2;

r is 0 or 1;

$R^1$ and $R^3$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^2$ is hydrogen, alkyl, substituted alkyl, alkoxy, substituted alkoxy, acyl, substituted acyl, acylamino, substituted acylamino, alkylamino, substituted alkylamino, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, dialkylamino, substituted dialkylamino, heteroalkyl, substituted heteroalkyl, heteroaryl, substituted heteroaryl, heteroarylalkyl, substituted heteroarylalkyl, oxycarbonyl or substituted oxycarbonyl, or optionally, $R^2$ and $R^3$ together with the atoms to which they are bonded form a cycloheteroalkyl or substituted cycloheteroalkyl ring;

$R^4$ and $R^5$ are independently hydrogen, alkyl, substituted alkyl, aryl, substituted aryl, arylalkyl, substituted arylalkyl, carbamoyl, substituted carbamoyl, cycloalkyl, substituted cycloalkyl, cycloalkoxycarbonyl, substituted cycloalkoxycarbonyl, heteroalkyl, substituted heteroalkyl, heteroaryl, substituted heteroaryl, heteroarylalkyl, substituted heteroarylalkyl, oxycarbonyl or substituted oxycarbonyl or optionally, $R^4$ and $R^5$ together with the carbon atom to which they are bonded form a cycloalkyl, substituted cycloalkyl, cycloheteroalkyl or substituted cycloheteroalkyl ring;

$R^6$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl; and each of $R^7$, $R^8$, $R^9$, $R^{10}$, $R^{11}$, $R^{12}$, $R^{13}$ and $R^{14}$ is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

In a second embodiment, the present invention provides a compound having structural Formula (II):

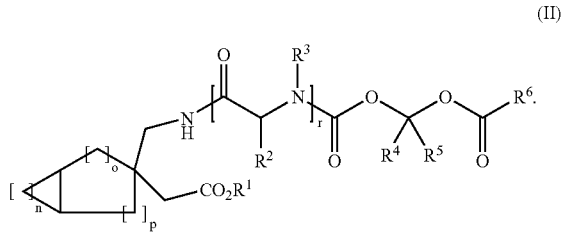

(II)

In a third embodiment, the present invention provides a compound having structural Formula (III):

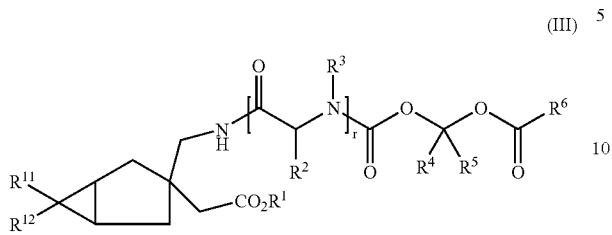

(III)

wherein each of $R^{11}$ and $R^{12}$ is independently hydrogen or methyl.

In a fourth embodiment, the present invention provides compounds of structural formula (III) derived from fused GABA analogs selected from the group consisting of (3-Aminomethyl-bicyclo[3.1.0]hex-3-yl)-acetic acid, (1α, 3α, 5α) (3-Aminomethyl-bicyclo[3.1.0]hex-3-yl)-acetic acid, (1α, 5β) (3-Aminomethyl-bicyclo[3.1.0]hex-3-yl)-acetic acid, (1α, 3β, 5α) (3-Aminomethyl-bicyclo[3.1.0]hex-3-yl)-acetic acid, ((1R, 5S)-3-Aminomethyl-6,6-dimethyl-bicyclo[3.1.0]hex-3-yl)-acetic acid and ((1S, 5R)-3-Aminomethyl-6,6-dimethyl-bicyclo[3.1.0]hex-3-yl)-acetic acid.

In a fifth embodiment, the present invention provides compounds having structural Formula (IV):

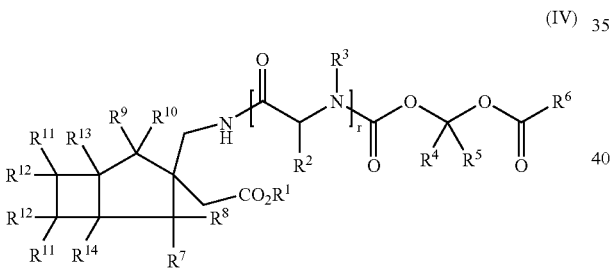

(IV)

wherein each of $R^7$, $R^8$, $R^9$, $R^{10}$, $R^{11}$, $R^{12}$, $R^{13}$ and $R^{14}$ is independently hydrogen or methyl.

In a sixth embodiment, the present invention provides compounds of structural Formula (IV) derived from fused GABA analogs selected from the group consisting of (3-Aminomethyl-bicyclo[3.2.0]hept-3-yl)-acetic acid, (1α, 3α, 5α) (3-Aminomethyl-bicyclo[3.2.0]hept-3-yl)-acetic acid, (1α, 5β) (3-Aminomethyl-bicyclo[3.2.0]hept-3-yl)-acetic acid, (1α, 3β, 5α) (3-Aminomethyl-bicyclo[3.2.0]hept-3-yl)-acetic acid, ((1R, 5S)-3-Aminomethyl-1,5-dimethyl-bicyclo[3.2.0]hept-3-yl)-acetic acid, ((1S, 5R)-3-Aminomethyl-1,5-dimethyl-bicyclo[3.2.0]hept-3-yl)-acetic acid, cis-((1S, 2R, 4S, 5R)-3-Aminomethyl-2,4-dimethyl-bicyclo[3.2.0]hept-3-yl)-acetic acid, trans-((1S, 2R, 4S, 5R)-3-Aminomethyl-2,4-dimethyl-bicyclo[3.2.0]hept-3-yl)-acetic acid, ((1S, 5R, 6S, 7R)-3-Aminomethyl-6,7-dimethyl-bicyclo[3.2.0]hept-3-yl)-acetic acid and ((1S, 5R, 6R, 7S)-3-Aminomethyl-6,7-dimethyl-bicyclo[3.2.0]hept-3-yl)-acetic acid.

In a seventh embodiment, the present invention provides compounds having structural Formula (V):

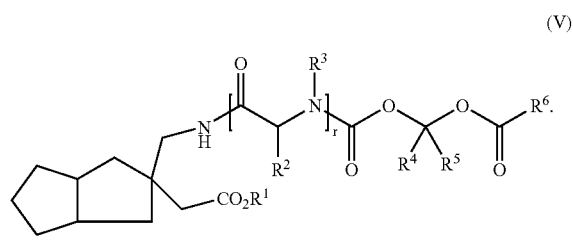

(V)

In a eighth embodiment, the present invention provides compounds of structural Formula (V) derived from fused GABA analogs selected from the group consisting of (2-Aminomethyl-octahydro-pentalen-2-yl)-acetic acid, (1α, 3α, 5α) (2-Aminomethyl-octahydro-pentalen-2-yl)-acetic acid, (1α, 5β) (2-Aminomethyl-octahydro-pentalen-2-yl)-acetic acid and (1α, 3β, 5α) (2-Aminomethyl-octahydro-pentalen-2-yl)-acetic acid.

In a ninth embodiment, the present invention provides compounds having structural Formula (VI):

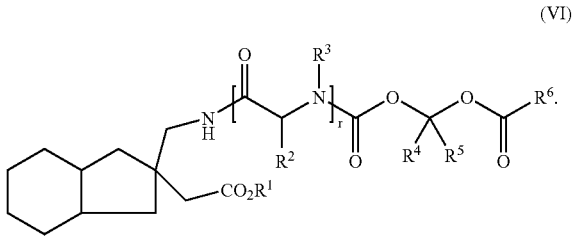

(VI)

In a tenth embodiment, the present invention provides compounds of structural Formula (VI) derived from fused GABA analogs selected from the group consisting of (2-Aminomethyl-octahydro-inden-2-yl)-acetic acid, (1αc, 6α, 8α) (2-Aminomethyl-octahydro-inden-2-yl)-acetic acid, (1α, 6β) (2-Aminomethyl-octahydro-inden-2-yl)-acetic acid and (1α, 6α, 8β) (2-Aminomethyl-octahydro-inden-2-yl)-acetic acid.

In a eleventh embodiment, the present invention provides compounds having structural Formula (VII):

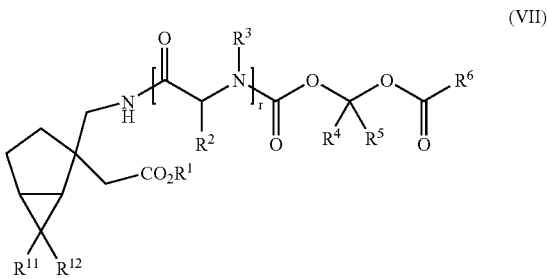

(VII)

wherein $R^{11}$ and $R^{12}$ are independently hydrogen or methyl.

In a twelfth embodiment, the present invention provides compounds of structural Formula (VII) derived from fused GABA analogs selected from the group consisting of (2-Aminomethyl-bicyclo[3.1.0]hex-2-yl)-acetic acid, ((1S, 2S, 5R)-2-Aminomethyl-bicyclo[3.1.0]hex-2-yl)-acetic acid, ((1R, 2S, 5S)-2-Aminomethyl-bicyclo[3.1.0]hex-2-yl)-acetic acid, ((1S, 2R, 5R)-2-Aminomethyl-bicyclo [3.1.0]hex-2-yl)-acetic acid, ((1R, 2R, 5S)-2-Aminomethyl-bicyclo[3.1.0]hex-2-yl)-acetic acid, (2-Aminomethyl-6,6-dimethyl-bicyclo[3.1.0]hex-2-yl)-acetic acid, ((1S, 2S, 5R)-2-Aminomethyl-6,6-dimethyl-bicyclo[3.1.0]hex-2-yl)-acetic acid, ((1R, 2S, 5S)-2-Aminomethyl-6,6-dimethyl-bicyclo[3.1.0]hex-2-yl)-acetic acid, ((1S, 2R, 5R)-2-Aminomethyl-6,6-dimethyl-bicyclo[3.1.0]hex-2-yl)-acetic acid and ((1R, 2R, 5S)-2-Aminomethyl-6,6-dimethyl-bicyclo[3.1.0]hex-2-yl)-acetic acid.

In a thirteenth embodiment, the present invention provides compounds having structural Formula (VIII):

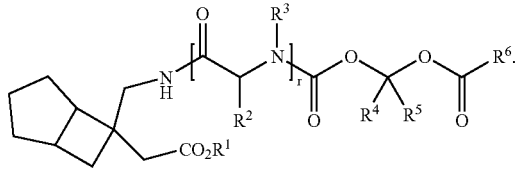

(VIII)

In a fourteenth embodiment, the present invention provides compounds of structural Formula (VIII) derived from fused GABA analogs selected from the group consisting of (6-Aminomethyl-bicyclo[3.2.0]hept-6-yl)-acetic acid, ((1R, 5R, 6S)-6-Aminomethyl-bicyclo[3.2.0]hept-6-yl)-acetic acid, ((1S, 5S, 6S)-6-Aminomethyl-bicyclo[3.2.0]hept-6-yl)-acetic acid, ((1R, 5R, 6R)-6-Aminomethyl-bicyclo[3.2.0]hept-6-yl)-acetic acid and ((1S, 5S, 6R)-6-Aminomethyl-bicyclo[3.2.0]hept-6-yl)-acetic acid.

In a fifteenth embodiment, the present invention provides compounds having structural Formula (IX):

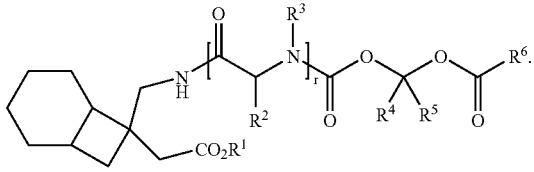

(IX)

In a sixteenth embodiment, the present invention provides compounds of structural Formula (IX) derived from fused GABA analogs selected from the group consisting of (7-Aminomethyl-bicyclo[4.2.0]oct-7-yl)-acetic acid, ((1R, 6R, 7S)-7-Aminomethyl-bicyclo[4.2.0]oct-7-yl)-acetic acid, ((1S, 6S, 7S)-7-Aminomethyl-bicyclo[4.2.0]oct-7-yl)-acetic acid, ((1R, 6R, 7R)-7-Aminomethyl-bicyclo[4.2.0]oct-7-yl)-acetic acid and ((1S, 6S, 7R)-7-Aminomethyl-bicyclo[4.2.0]oct-7-yl)-acetic acid.

In a seventeenth embodiment, the present invention provides compounds of structural Formula (X):

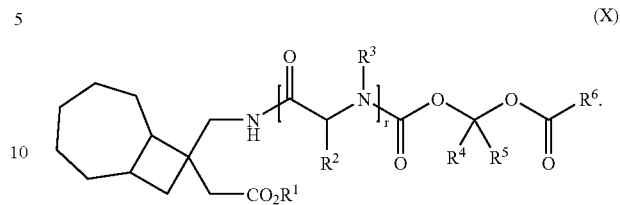

(X)

In a eighteenth embodiment, the present invention provides compounds of structural Formula (X) derived from fused GABA analogs selected from the group consisting of (1R, 7R, 8S)-8-aminomethyl-bicyclo[5.2.0]non-8-yl)-acetic acid, ((1S, 7S, 8S)-8-aminomethyl-bicyclo[5.2.0]non-8-yl)-acetic acid, ((1R, 7R, 8R)-8-aminomethyl-bicyclo[5.2.0] non-8-yl)-acetic acid and ((1S, 7S, 8R)-8-aminomethyl-bicyclo[5.2.0]non-8-yl)-acetic acid.

Preferably, in the above embodiments, $R^1$ is hydrogen. Alternatively, $R^1$ may be hydrogen, alkanyl, substituted alkanyl, alkenyl, substituted alkenyl, aryl, substituted aryl, arylalkyl or substituted arylalkyl. Preferably, $R^1$ is hydrogen, methyl, ethyl, benzyl, —C(CH$_3$)=CH$_2$, —CH$_2$C(O)N (CH$_3$)$_2$,

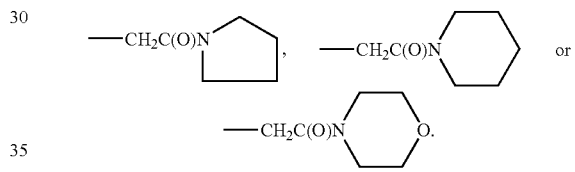

Preferably, in the eighteen embodiments above, $R^2$ is hydrogen, alkanyl, substituted alkanyl, aryl, substituted aryl, arylalkanyl, substituted arylalkanyl, cycloalkanyl, heteroarylalkyl or substituted heteroarylalkanyl. More preferably, $R^2$ is hydrogen, alkanyl or cycloalkanyl. Even more preferably, $R^2$ is selected from the group consisting of hydrogen, methyl, isopropyl, isobutyl, sec-butyl, t-butyl, cyclopentyl and cyclohexyl.

Preferably, in the first eighteen embodiments above, $R^2$ is selected from the group consisting of substituted alkanyl. More preferably, $R^2$ is selected from the group consisting of —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ and —CH$_2$CH$_2$CH$_2$NHC(NH)NH$_2$.

Preferably, in the first eighteen embodiments above, $R^2$ is selected from the group consisting of aryl, arylalkanyl, substituted arylalkanyl and heteroarylalkanyl. More preferably, $R^2$ is selected from the group consisting of phenyl, benzyl, 4-hydroxybenzyl, 4-bromobenzyl, 4-imidazolylmethyl and 3-indolylmethyl.

Preferably, in the first eighteen embodiments above, $R^2$ and $R^3$ together with the atoms to which they are bonded form a cycloheteroalkyl or substituted cycloheteroalkyl ring. More preferably, $R^2$ and $R^3$ together with the atoms to which they are bonded form an azetidine, pyrrolidine or piperidine ring. Preferably, in the first eighteen embodiments above, $R^3$ is hydrogen, alkyl, substituted alkyl, arylalkyl or substituted arylalkyl. More preferably, $R^3$ is hydrogen, methyl, ethyl or benzyl.

Preferably, in the first eighteen embodiments above, $R^4$ and $R^5$ are independently hydrogen, alkyl, substituted alkyl, alkoxycarbonyl, substituted alkoxycarbonyl, aryl, substituted aryl, arylalkyl, substituted arylalkyl, heteroaryl or substituted heteroaryl. More preferably, $R^4$ and $R^5$ are independently hydrogen, alkyl, alkoxycarbonyl, aryl, arylalkyl or heteroaryl. Most preferably, $R^4$ and $R^5$ are independently hydrogen, methyl, ethyl, propyl, isopropyl, sec-butyl, tert-butyl, cyclopentyl, cyclohexyl, phenyl, benzyl, phenethyl, 3-pyridyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl or cyclohexyloxycarbonyl.

Preferably, in the first eighteen embodiments above, $R^6$ is acyl, substituted acyl, alkyl, substituted alkyl, aryl, substituted aryl, arylalkyl, substituted arylalkyl, cycloalkyl, substituted cycloalkyl, heteroaryl or substituted heteroaryl. More preferably, $R^6$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

Preferably, in the first embodiment above, each of $R^7$, $R^8$, $R^9$, $R^{10}$, $R^{11}$, $R^{12}$, $R^{13}$ and $R^{14}$ is independently hydrogen, alkyl or substituted alkyl. More preferably, each of $R^7$, $R^8$, $R^9$, $R^{10}$, $R^{11}$, $R^{12}$, $R^{13}$ and $R^{14}$ is independently hydrogen or methyl.

Preferably, in the first eighteen embodiments above, $R^1$ is hydrogen and $R^2$ and $R^3$ together with the atoms to which they are attached form a pyrrolidine ring. Preferably, in this embodiment, $R^1$ is hydrogen. Alternatively, $R^1$ is methyl, ethyl, benzyl, —C(CH$_3$)═CH$_2$, —CH$_2$C(O)N(CH$_3$)$_2$,

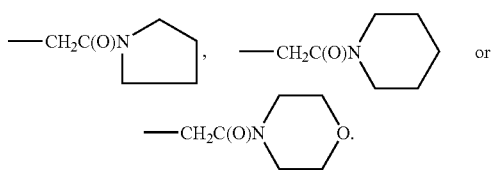

Preferably, in the first eighteen embodiments above, $R^3$ is hydrogen and $R^2$ is selected from the group consisting of hydrogen, methyl, 2-propyl, 2-butyl, isobutyl, tert-butyl, cyclopentyl, cyclohexyl, phenyl, benzyl, 4-hydroxybenzyl, 4-bromobenzyl, 4-imidazolylmethyl, 3CH$_2$OH, CH(OH)CH$_3$, -CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ and —CH$_2$CH$_2$CH$_2$NHC(NH)NH$_2$. Preferably, in this embodiment, $R^1$ is hydrogen. Alternatively, $R^1$ is methyl, ethyl, benzyl, —C(CH$_3$)═CH$_2$, —CH$_2$C(O)N(CH$_3$)$_2$,

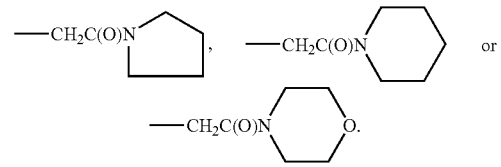

Preferably, in the first eighteen embodiments above, $R^1$ is hydrogen, alkanyl, substituted alkanyl, alkenyl, substituted alkenyl, aryl, substituted aryl, arylalkyl or substituted arylalkyl, $R^2$ is hydrogen, alkanyl, substituted alkanyl, aryl, substituted aryl, arylalkanyl, substituted arylalkanyl, cycloalkanyl, heteroarylalkyl or substituted heteroarylalkanyl or optionally $R^2$ and $R^3$ together with the atoms to which they are bonded form a cycloheteroalkyl or substituted cycloheteroalkyl ring, $R^3$ is hydrogen, alkyl, substituted alkyl, arylalkyl or substituted arylalkyl, $R^4$ and $R^5$ are independently hydrogen, alkyl, substituted alkyl, alkoxycarbonyl, substituted alkoxycarbonyl, aryl, substituted aryl, arylalkyl, substituted arylalkyl, heteroaryl or substituted heteroaryl and $R^6$ is acyl, substituted acyl, alkyl, substituted alkyl, aryl, substituted aryl, arylalkyl, substituted arylalkyl, cycloalkyl, substituted cycloalkyl, heteroaryl or substituted heteroaryl.

Preferably, in the first eighteen embodiments above, r is 0, $R^4$ is methyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is ethyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is propyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is isopropyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is butyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl; cyclopentyl, cyclohexyl and 3-pyridyl.

Preferably, in the first eighteen embodiments above, r is 0, $R^4$ is isobutyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is sec-butyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is tert-butyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-diethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen-embodiments above, r is 0, $R^4$ is cyclopentyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is cyclohexyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is phenyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is benzyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is phenethyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is 3-pyridyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is methyl, $R^5$ is methyl, $R^1$ is hydrogen and $R^6$ is selected from the group consisting of methyl, ethyl, propyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is methoxycarbonyl, $R^5$ is methyl, $R^1$ is hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is ethoxycarbonyl, $R^5$ is methyl, $R^1$ is hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^3$ is propoxycarbonyl, $R^4$ is methyl, $R^1$ is hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is isopropoxycarbonyl, $R^5$ is methyl, $R^1$ is hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is butoxycarbonyl, $R^5$ is methyl, $R^1$ is hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is isobutoxycarbonyl, $R^5$ is methyl, $R^1$ is hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is sec-butoxycarbonyl, $R^5$ is methyl, $R^1$ is hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is tert-butoxycarbonyl, $R^5$ is methyl, $R^1$ is hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, $R^4$ is cyclohexyloxycarbonyl, $R^5$ is methyl, $R^1$ is hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, r is 0, each of $R^1$, $R^4$ and $R^5$ is hydrogen, and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

Preferably, in the first eighteen embodiments above, $R^3$ is hydrogen, and $R^2$ is selected from the group consisting of hydrogen, methyl, 2-propyl, 2-butyl, isobutyl, tert-butyl, cyclopentyl, cyclohexyl, phenyl, benzyl, 4-hydroxybenzyl, 4-bromobenzyl, 4-imidazolylmethyl, 3-indolylmethyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$ and —$CH_2CH_2CH_2NHC(NH)NH_2$.

4.3 Synthesis of the Compounds of the Invention

Those of skill in the art will appreciate that a preferred synthetic route to the compounds of the invention will consist of attaching promoieties to fused GABA analogs. Methods have been described in the art for the synthesis of fused GABA analogs (Blakemore et al., International Publication No. WO 02/085839; Blakemore et al., International Publication No. WO 02/090318; and Bryans et al., International Publication No. WO 01/28978). Other methods will be apparent to the skilled artisan for synthesizing fused GABA analogs in view of the references provided above. The promoieties described herein, are known in the art and may be prepared and attached to fused GABA analogs by established procedures (See e.g., Green et al., "Protective Groups in Organic Chemistry", (Wiley, $2^{nd}$ ed. 1991); Harrison et al., "Compendium of Synthetic Organic Methods", Vols. 1–8 (John Wiley and Sons, 1971–1996; Larock "Comprehensive Organic Transformations," VCH Publishers, 1989; and Paquette, "Encyclopedia of Reagents for Organic Synthesis," John Wiley & Sons, 1995). Preferably, the promoieties illustrated herein, may be attached to fused GABA analogs by the procedures described in Cundy et al., U.S. patent application Ser. No. 10/710,127; Gallop et al., U.S. patent application Ser. No. 10/171,485; and Gallop et al., U.S. patent application Ser. No. 10/167,197.

4.4 Therapeutic Uses

In accordance with the invention, a compound and/or pharmaceutical composition of the invention is administered to a patient, preferably a human, suffering from epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders, hot flashes, restless legs syndrome, urinary incontinence or ethanol withdrawal syndrome. Further, in certain embodiments, the compounds and/or pharmaceutical compositions of the invention are administered to a patient, preferably a human, as a preventative measure against various diseases or disorders. Thus, the compounds and/or pharmaceutical compositions of the invention may be administered as a preventative measure to a patient having a predisposition for epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders, hot flashes, restless legs syndrome, urinary incontinence and ethanol withdrawal syndrome. Accordingly, the compounds and/or pharmaceutical compositions of the invention may be used for the prevention of one disease or disorder and concurrently treating another (e.g., prevention of psychosis while treating gastrointestinal disorders; prevention of neuropathic pain while treating ethanol withdrawal syndrome).

The suitability of the compounds and/or pharmaceutical compositions of the invention in treating or preventing epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders, hot flashes, restless legs syndrome, urinary incontinence and ethanol withdrawal syndrome may be determined by methods described in the art (See, e.g., Satzinger et al., U.S. Pat. No. 4,024,175; Satzinger et al., U.S. Pat. No. 4,087,544; Woodruff, U.S. Pat. No. 5,084,169; Silverman et al., U.S. Pat. No. 5,563,175; Singh, U.S. Pat. No. 6,001,876; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Magnus-Miller et al., International Publication No. WO 99/37296; Bryans et al., International Publication No. WO 99/31075; Bryans et al., International Publication No. WO 99/61424; Pande, International Publication No. WO 00/23067; Bryans, International Publication No. WO 00/31020; Bryans et al., International Publication No. WO 00/50027; Bryans et al, International Publication No. WO 02/00209; Bryans et al., International Publication No. WO 01/28978 and Blakemore et al., International Publication No. WO 02/085839).

Accordingly, it is well with the capability of those of skill in the art to assay and use the compounds of the invention and/or pharmaceutical compositions thereof to treat or prevent the above diseases or disorders.

4.5 Therapeutic/Prophylactic Administration

The compounds and/or pharmaceutical compositions of the invention may be advantageously used in human medicine. As previously described in Section 4.4 above, compounds and/or pharmaceutical compositions of the invention are useful for the treatment or prevention of epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), arthritis, insomnia, gastrointestinal disorders, hot flashes, restless legs syndrome, urinary incontinence, insomnia, gastrointestinal disorders or ethanol withdrawal syndrome.

When used to treat or prevent the above disease or disorders compounds and/or pharmaceutical compositions of the invention may be administered or applied singly, in combination with other agents. The compounds and/or pharmaceutical compositions of the invention may also be administered or applied singly, in combination with other pharmaceutically active agents, including other compounds and/or pharmaceutical compositions of the invention.

The current invention provides methods of treatment and prophylaxis by administration to a patient of a therapeutically effective amount of a pharmaceutical composition or compound of the invention. The patient may be an animal, is more preferably a mammal, and most preferably a human.

The present compounds and/or pharmaceutical compositions of the invention, which comprise one or more compounds of the invention, are preferably administered orally. The compounds and/or pharmaceutical compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

In particularly preferred embodiments, the compounds and/or pharmaceutical compositions of the invention can be delivered via sustained release systems, preferably oral sustained release systems. In one embodiment, a pump may be used (Langer, supra; Sefton, 1987, *CRC Crit Ref Biomed. Eng.* 14:201; Saudek et al., 1989, *N. Engl. J Med.* 321:574).

In another embodiment polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J Macromol. Sci. Rev. Macromol Chem.* 23:61; Levy et al., 1985, *Science* 228: 190; During et al., 1989, *Ann. Neurol.* 25:351; Howard et al., 1989, *J. Neurosurg.* 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described (Alderman, *Int. J. Pharm. Tech. & Prod. Mfr.,* 1984, 5(3) 1–9). Factors affecting drug release are well known to the skilled artisan and have been described in the art (Bamba et al., *Int. J. Pharm.,* 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another embodiment, osmotic delivery systems are used for oral sustained release administration (Verma et al., *Drug Dev. Ind. Pharm.,* 2000, 26:695–708). In a preferred embodiment, OROS™ osmotic devices are used for oral sustained release delivery devices (Theeuwes et al., U.S. Pat. No. 3,845,770; Theeuwes et al., U.S. Pat. No. 3,916,899).

In yet another embodiment, a controlled-release system can be placed in proximity of the target of the compounds and/or pharmaceutical compositions of the invention, thus requiring only a fraction of the systemic dose (See, e.g., Goodson, in "Medical Applications of Controlled Release," supra, vol. 2, pp. 115–138 (1984)). Other controlled-release systems discussed in Langer, 1990, *Science* 249:1527–1533 may also be used.

The compounds and/or pharmaceutical compositions of the invention preferably provide fused GABA analogs upon in vivo administration to a patient. While not wishing to be bound by theory, the promoiety or promoieties of the compounds and/or pharmaceutical compositions of the invention may be cleaved either chemically and/or enzymatically. One or more enzymes present in the stomach, intestinal lumen, intestinal tissue, blood, liver, brain or any other suitable tissue of a mammal may enzymatically cleave the promoiety or promoieties of the compounds and/or compositions of the invention. The mechanism of cleavage is not important to the current invention.

While not wishing to bound by theory, the promoiety or promoieties of the compounds and/or pharmaceutical compositions of the invention may be cleaved prior to absorption by the gastrointestinal tract (e.g., within the stomach or intestinal lumen) and/or after absorption by the gastrointestinal tract (e.g., in intestinal tissue, blood, liver or other suitable tissue of a mammal). If the promoiety or promoieties of the compounds of the invention are cleaved prior to absorption by the gastrointestinal tract, the resulting fused GABA analogs may be absorbed into the systemic circulation conventionally (e.g. via amino acid transporter(s) located in the small intestine). If the promoiety or promoieties of the compounds of the invention are cleaved after absorption by the gastrointestinal tract, these fused GABA analog prodrugs may have the opportunity to be absorbed into the systemic circulation either by passive diffusion, active transport or by both passive and active processes.

If the promoiety or promoieties of the compounds of the invention are cleaved after absorption by the gastrointestinal tract, these fused GABA analog prodrugs may have the opportunity to be absorbed into the systemic circulation from the large intestine. In this situation, the compounds and/or pharmaceutical compositions of the invention are preferably administered as sustained release systems. In a preferred embodiment, the compounds and/or pharmaceutical compositions of the invention are delivered by oral sustained release administration. Preferably, in this embodiment, the compounds and/or pharmaceutical compositions of the invention are administered twice per day (more preferably, once per day).

4.6 Pharmaceutical Compositions

The present pharmaceutical compositions contain a therapeutically effective amount of one or more compounds of the invention, preferably, in purified form, together with a suitable amount of a pharmaceutically acceptable vehicle, to provide the form for proper administration to a patient. When administered to a patient, the compounds of the invention and pharmaceutically acceptable vehicles are preferably sterile. Water is a preferred vehicle when a compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (e.g., Grosswald et al., U.S. Pat. No. 5,698,155). Other examples of suitable pharmaceutical vehicles have been described in the art (see, Remington's Pharmaceutical Sciences, Philadelphia College of Pharmacy and Science, 19th Edition, 1995). Preferred compositions of the invention are formulated for oral delivery, particularly for oral sustained release administration.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds and pharmaceutical compositions of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

Compositions for administration via other routes may also be contemplated. For buccal administration, the compositions may take the form of tablets, lozenges, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound of the invention may also be formulated in rectal or vaginal compositions such as suppositories or retention enemas, e.g., containing conventional suppository bases such as cocoa butter or other glycerides. In addition to the formulations described previously, a compound of the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

4.7 Therapeutic Doses

A compound of the invention and/or pharmaceutical compositions thereof, will generally be used in an amount effective to achieve the intended purpose. For use to treat or prevent diseases or disorders such as epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders, hot flashes, restless legs syndrome, urinary incontinence or ethanol withdrawal syndrome, the compounds of the invention and/or pharmaceutical compositions thereof, are administered or applied in a therapeutically effective amount.

The amount of a compound of the invention and/or pharmaceutical composition thereof that will be effective in the treatment of a particular disorder or condition disclosed herein will depend on the nature of the disorder or condition, and can be determined by standard clinical techniques known in the art. In addition, in vitro or in vivo assays may optionally be employed to help identify optimal dosage ranges. The amount of a compound of the invention and/or pharmaceutical composition thereof administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In a preferred embodiment, the compounds of the invention and/or pharmaceutical compositions thereof are delivered by oral sustained release administration. Preferably, in this embodiment, the compounds of the invention and/or pharmaceutical compositions thereof are administered twice per day (more preferably, once per day). Dosing may be repeated intermittently, may be provided alone or in combination with other drugs and may continue as long as required for effective treatment of the disease state or disorder.

Suitable dosage ranges for oral administration are dependent on the potency of the parent fused GABA analog, but are generally about 0.001 mg to about 200 mg of a compound of the invention per kilogram body weight. Other fused GABA analogs may be more potent and lower doses may be appropriate for both the parent drug and any prodrug (measured on an equivalent molar basis). Dosage ranges may be readily determined by methods known to the skilled artisan.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for reducing convulsion. The compounds of the invention and/or pharmaceutical compositions thereof may also be demonstrated to be effective and safe using animal model systems.

Preferably, a therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the invention described herein will preferably be within a range of circulating concentrations that include an effective dose with little or no toxicity.

4.8 Combination Therapy

In certain embodiments of the present invention, the compounds of the invention and/or pharmaceutical compositions thereof can be used in combination therapy with at least one other therapeutic agent. The compound of the invention and/or pharmaceutical composition thereof and the therapeutic agent can act additively or, more preferably, synergistically. In a preferred embodiment, a compound of the invention and/or a pharmaceutical composition thereof is administered concurrently with the administration of another therapeutic agent. In another embodiment, a compound of the invention and/or pharmaceutical composition thereof is administered prior or subsequent to administration of another therapeutic agent.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

What is claimed is:

1. A compound of structural formula (I):

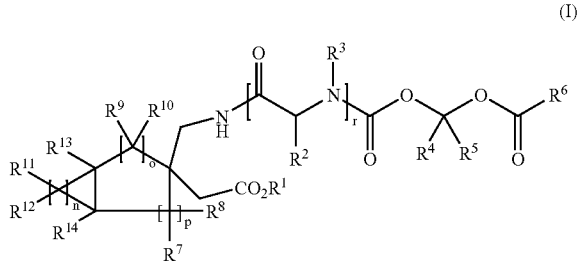

or a pharmaceutically acceptable salt, hydrate, solvate or N-oxide thereof, wherein:
  n is 1, 2, 3, 4, 5 or 6;
  o is 0, 1, 2 or 3;
  p is 0, 1 or 2;
  r is 0 or 1;
  $R^1$ and $R^3$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;
  $R^2$ is hydrogen, alkyl, substituted alkyl, alkoxy, substituted alkoxy, acyl, substituted acyl, acylamino, substituted acylamino, alkylamino, substituted alkylamino, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, dialkylamino, substituted dialkylamino, heteroalkyl, substituted heteroalkyl, heteroaryl, substituted heteroaryl, heteroarylalkyl, substituted heteroarylalkyl, oxycarbonyl or substituted oxycarbonyl, or optionally, $R^2$ and $R^3$ together with the atoms to which they are bonded form a cycloheteroalkyl or substituted cycloheteroalkyl ring;
  $R^4$ and $R^5$ are independently hydrogen, alkyl, substituted alkyl, aryl, substituted aryl, arylalkyl, substituted arylalkyl, carbamoyl, substituted carbamoyl, cycloalkyl, substituted cycloalkyl, cycloalkoxycarbonyl, substituted cycloalkoxycarbonyl, heteroalkyl, substituted heteroalkyl, heteroaryl, substituted heteroaryl, heteroarylalkyl, substituted heteroarylalkyl, oxycarbonyl or substituted oxycarbonyl or optionally, $R^4$ and $R^5$ together with the carbon atom to which they are bonded form a cycloalkyl, substituted cycloalkyl, cycloheteroalkyl or substituted cycloheteroalkyl ring;
  $R^6$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl; and
  each of $R^7$, $R^8$, $R^9$, $R^{10}$, $R^{11}$, $R^{12}$, $R^{13}$ and $R^{14}$ is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

2. The compound of claim 1, wherein each of $R^7$, $R^8$, $R^9$, $R^{10}$, $R^{11}$, $R^{12}$, $R^{13}$ and $R^{14}$ is independently hydrogen, alkyl or substituted alkyl.

3. The compound of claim 2, wherein $R^7$, $R^8$, $R^9$, $R^{10}$, $R^{11}$, $R^{12}$, $R^{13}$ and $R^{14}$ are hydrogen or methyl.

4. The compound of claim 1, wherein:
  $R^1$ is hydrogen, alkanyl, substituted alkanyl, alkenyl, substituted alkenyl, aryl, substituted aryl, arylalkyl or substituted arylalkyl;
  $R^2$ is hydrogen, alkanyl, substituted alkanyl, aryl, substituted aryl, arylalkanyl, substituted arylalkanyl, cycloalkanyl, heteroarylalkanyl or substituted heteroarylalkanyl or optionally $R^2$ and $R^3$ together with the atoms to which they are bonded form a cycloheteroalkyl or substituted cycloheteroalkyl ring;
  $R^3$ is hydrogen, alkyl, substituted alkyl, arylalkyl or substituted arylalkyl;
  $R^4$ and $R^5$ are independently hydrogen, alkyl, substituted alkyl, alkoxycarbonyl, substituted alkoxycarbonyl, aryl, substituted aryl, arylalkyl, substituted arylalkyl, heteroaryl or substituted heteroaryl;
  $R^6$ is acyl, substituted acyl, alkyl, substituted alkyl, aryl, substituted aryl, arylalkyl, substituted arylalkyl, cycloalkyl, substituted cycloalkyl, heteroaryl or substituted heteroaryl; and
  each of $R^7$, $R^8$, $R^9$, $R^{10}$, $R^{11}$, $R^{12}$, $R^{13}$ and $R^{14}$ is independently hydrogen, alkyl or substituted alkyl.

5. The compound of claim 4, having structural Formula (IV):

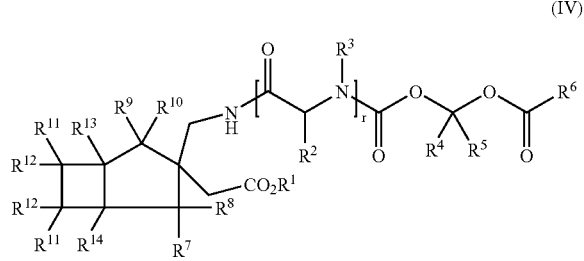

wherein each of $R^7$, $R^8$, $R^9$, $R^{10}$, $R^{11}$, $R^{12}$, $R^{13}$ and $R^{14}$ is independently hydrogen or methyl.

6. The compound of claim 5, wherein the compound is derived from a fused GABA analog selected from the group consisting of:
(1α, 3α, 5α)(3-Aminomethyl-bicyclo[3.2.0]hept-3-yl)-acetic acid; and
(1α, 3β, 5α)(3-Aminomethyl-bicyclo[3.2.0]hept-3-yl)-acetic acid.

7. The compound of claim 4 having structural Formula (VIII):

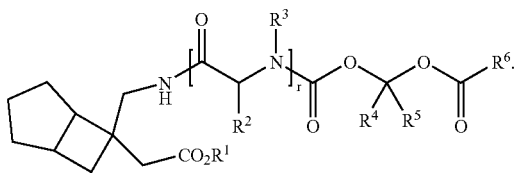

(VIII)

8. The compound of claim 7, wherein the compound is derived from a fused GABA analog selected from the group consisting of:
(6-Aminomethyl-bicyclo[3.2.0]hept-6-yl)-acetic acid;
((1R, 5R, 6S)-6-Aminomethyl-bicyclo[3.2.0]hept-6-yl)-acetic acid; and
((1S, 5S, 6R)-6-Aminomethyl-bicyclo[3.2.0]hept-6-yl)-acetic acid.

9. The compound of claim 4, having structural Formula (IX):

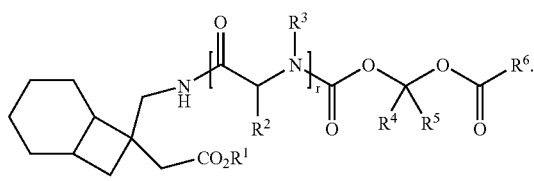

(IX)

10. The compound of any one of claims 4–9, wherein r is 0, $R^4$ is methyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

11. The compound of any one of claims 4–9, wherein r is 0, $R^4$ is ethyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

12. The compound of any one of claims 4–9, wherein r is 0, $R^4$ is propyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

13. The compound of any one of claims 4–9, wherein r is 0, $R^4$ is isopropyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

14. The compound of any one of claims 4–9, wherein r is 0, $R^4$ is butyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

15. The compound of any one of claims 4–9, wherein r is 0, $R^4$ is isobutyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

16. The compound of any one of claims 4–9, wherein r is 0, $R^4$ is sec-butyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

17. The compound of any one of claims 4–9, wherein r is 0, $R^4$ is cyclopentyl; $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

18. The compound of any one of claims 4–9, wherein r is 0, $R^4$ is cyclohexyl, $R^1$ and $R^5$ are hydrogen and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

19. The compound of any one of claims 4–9, wherein r is 0, each of $R^1$, $R^4$ and $R^5$ is hydrogen, and $R^6$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl.

20. A method for treating or preventing epilepsy, depression, anxiety, psychosis, faintness attacks, hypokinesia, cranial disorders, neurodegenerative disorders, panic, pain, inflammatory disease, insomnia, gastrointestinal disorders or ethanol withdrawal syndrome in a patient, comprising administering to a patient in need of such treatment a therapeutically effective amount of a compound according to claim 1.

21. A method for treating or preventing neuropathic pain, muscular pain or skeletal pain in a patient, comprising administering to a patient in need of such treatment a therapeutically effective amount of a compound according to claim 1.

22. A pharmaceutical composition for treating or preventing epilepsy, depression, anxiety, psychosis, faintness attacks, hypokinesia, cranial disorders, neurodegenerative disorders, panic, pain, inflammatory disease, insomnia, gastrointestinal disorders or ethanol withdrawal syndrome in a patient, comprising a therapeutically effective amount of a compound according to claim 1 and a pharmaceutically acceptable vehicle.

* * * * *